United States Patent [19]
Shibata

[11] Patent Number: 5,605,630
[45] Date of Patent: Feb. 25, 1997

[54] BLOOD FLOW DIRECTION CHANGEOVER DEVICE AND METHOD FOR HEMODIALYZER

[75] Inventor: Takeru Shibata, Yokohama, Japan

[73] Assignee: Scitec Kabushiki Kaisha, Kamakura, Japan

[21] Appl. No.: 202,265

[22] Filed: Feb. 25, 1994

[51] Int. Cl.$^6$ ............................ B01D 61/00; B01D 61/28; B01D 61/32

[52] U.S. Cl. .................... 210/646; 210/143; 210/321.72; 210/420; 210/424; 210/645

[58] Field of Search ..................................... 210/645, 646, 210/739, 87, 97, 98, 117, 134, 136, 143, 195.1, 321.69, 321.72, 420, 424; 604/4, 5; 137/1, 625; 422/103

[56] References Cited

U.S. PATENT DOCUMENTS

| | | | |
|---|---|---|---|
| 4,324,662 | 4/1982 | Schnell | 210/646 |
| 4,331,540 | 5/1982 | Witsoe | 210/646 |
| 4,614,590 | 9/1986 | Rath et al. | 210/646 |
| 4,623,450 | 11/1986 | Vantard et al. | 210/87 |
| 4,648,866 | 3/1987 | Malbrancq et al. | 210/195.2 |
| 4,834,888 | 5/1989 | Polaschegg | 210/646 |
| 4,844,810 | 7/1989 | Richalley et al. | 210/646 |

FOREIGN PATENT DOCUMENTS

| | | |
|---|---|---|
| 62-54510 | 11/1987 | Japan . |
| 63-100051 | 6/1988 | Japan . |
| 1-267833 | 10/1989 | Japan . |
| 2-213702 | 8/1990 | Japan . |

Primary Examiner—John Kim
Attorney, Agent, or Firm—Wenderoth, Lind & Ponack

[57] ABSTRACT

Blood guided out of the artery of a patient by a blood pump is introduced into an arterial inlet of a blood flow direction changeover device, and it is then guided from the outlet of the changeover device to a dialzyer through an inlet thereof. The blood then leaves an outlet of the dialyzer, enters the blood flow path changeover device, leaves a venous outlet of the changeover device and returns into the vein of the patient. The dialytic liquid, on the other hand, leaves a dialytic liquid outlet, passes through a dialytic liquid flow direction changeover device and is finally discharged through a dialytic liquid outlet. Then, the respective changeover devices are changed over to reverse the respective flows. This is intermittently repeated. Thus, blood coagulation can be inhibited or prevented.

3 Claims, 3 Drawing Sheets

BLOOD FLOW DIRECTION CHANGEOVER DEVICE AND METHOD FOR HEMODIALYZER

BACKGROUND OF THE INVENTION

1. Field of the Invention

The present invention relates generally to medical care and specifically to hemodialysis. More particularly, this invention concerns a device and method for feeding blood and dialytic liquid to a hemodialyzer.

2. Prior Art

For blood dialysis using a hollow fiber type of blood dialyzer, the flows of the blood and dialytic liquid passing through the dialyzer are fixed from the beginning to the end of dialysis. Usually, the dialyzer is provided with a red mark on the blood inlet port (the arterial header) and with a blue mark on the blood outlet port (the venous header). The inlet and outlet ports for dialytic liquid, on the other hand, are not particularly provided with any color mark but, in order to obtain sufficient dialytic efficiency, the dialytic liquid is generally passed countercurrently with respect to the blood.

In starting hemodialysis, the arterial and venous circuits of the blood circulation path are respectively connected to the arterial and venous blood ports of a dialyzer, and feed and discharge hoses for dialytic liquid are respectively coupled to the dialytic liquid inlet and outlet in the dialyzer. Thus, it is most unlikely that the blood circuits and dialytic liquid hoses, once connected to the associated ports, are removed from the dialyzer in the course of dialysis. In particular, it is impossible to attach and detach the blood circuits under dialysis to and from the dialyzer.

In the blood inlet and outlet ports or headers of a hollow fiber type of dialyzer, the blood is most likely to coagulate. This is because, where the blood is fed through a constricted inlet in a blood feeder to the inlet header having a large space, the blood is likely to stagnate due to the fact that the flow of the blood there suddenly becomes slow. This is also true of the outlet header.

So far, various approaches to preventing blood coagulation through the header portions have been proposed. For instance, some approaches have been set forth in Japanese Patent No. 1267833, JP-B-62-54510, JP-U-63-100051, etc., that are directed to improving the configurations of the header portions. However, all these approaches intended for improving header configurations are found to fail to solve the problem of blood coagulation problem through the header portions for various reasons, for instance, due to the facts that the quantity of the blood treated by actual dialysis lies in a wide range of 100 to 300 ml per minute, there is a difference in blood viscosity from person to person, and the blood viscosity changes overtime during the course of dialysis.

In order to re-use this dialyzer, it must be removed from its circuit and then cleaned by washing with special equipment.

Blood is likely to coagulate upon contact with foreign matter outside the body. Blood coagulation takes place outside the body, especially where the circulation flow of the blood becomes stagnant or slow. In the case of hemodialysis with a hollow fiber type of dialyzer, blood coagulation is likely to take place in a blood inlet header D-1 and a blood outlet header D-2 of a dialyzer 3 shown in FIG. 3. When the blood flows through the narrow inlet of 3 to 4 mm in inner diameter into the wide space of 20 to 60 mm in inner diameter, its flow suddenly becomes slow. In addition, the central blood stream flows linearly into fine, hollow fibers of about 200 µm in inner diameter, but the blood flow is likely to stagnate on the periphery of the header, so that the blood can start to coagulate in a ring form from the periphery of the header. This blood coagulation then grows in the radially inward direction. In the hollow fibers that are clogged up by the coagulated blood layer, the inside blood will further tend to coagulate because the blood is not allowed to flow freely. Through the outlet header D-2, if not comparable to the inlet header, there is some blood coagulation on the periphery, again because there is a slow blood flow.

Blood, when there is less change in its flow pattern, is likely to coagulate early where its flow remains stagnant. The prevention of blood coagulation by varying the flow speed of blood and changing the flow pattern intermittently has already been proposed in JP-A-2-213702.

For recycling this dialyzer, it must be removed from its circuit. However, unless it is treated with the greatest care, it will be contaminated with various bacteria. In addition, this will possibly expose those who are engaged in medical care to a risk of bacterial infection.

A main object of the invention is to improve the approaches so far proposed by drastically changing a blood flow pattern to a dialyzer. According to the invention, this is achieved by intermittently changing the direction of blood flow to a dialyzer to the countercurrent direction, thereby preventing or inhibiting blood coagulation. In the process of blood coagulation, the blood's coagulating ingredients, fibrin and platelets, start to be deposited onto the periphery of the header and the surface of hollow fibers, and blood coagulation grows large around the deposits serving as nucleuses. According to the invention, the intermittent inversion of the blood flow direction enables such deposits to be peeled off, and this is much more effective for the prevention of blood coagulation than would be possible with a change in the blood flow pattern achieved merely by changing the speed of blood.

SUMMARY OF THE INVENTION

According to one aspect of the invention, there is provided a device for changing over the direction of a blood flow to a hemodialzyer unit, comprising in combination:

a dialyzer, a blood circuit coupled to the dialyzer, blood flow direction changeover means that is attached to the blood circuit for changing over the direction of the blood flow through the dialyzer from one direction to the other, control means for placing the blood flow changeover means under intermittent changeover control, and a dialytic liquid circuit for feeding fresh dialytic liquid to the dialyzer.

According to another aspect of the invention, there is provided a method for changing over the direction of a blood flow to a hemodialyzer unit, wherein blood flow changeover means is coupled to a blood circuit connected to a dialyzer, thereby intermittently changing over the direction of the blood flow through the dialyzer from one direction to the other.

According to the third aspect of the invention, there is provided a device for changing over the direction of a blood flow to a hemodialzyer unit, comprising in combination:

a dialyzer, a blood circuit coupled to the dialyzer, blood flow direction changeover means that is attached to the blood circuit for changing over the direction of the blood flow through the dialyzer from one direction to the other, control means for placing the blood flow changeover means under intermittent changeover control, a dialytic liquid circuit for feeding fresh dialytic liquid to the dialyzer, a thrombus inflow-preventing filter that is located at an outlet in the blood circuit or in the vicinity of a position through which the dialyzed blood returns into the body, and a bacterium-elimination or pyrogenic filter that is located in the vicinity of an inlet in the dialytic liquid circuit.

According to the fourth aspect of the invention, there is provided a device for changing over the direction of a blood flow to a hemodialzyer unit, comprising in combination:

a dialyzer, a blood circuit coupled to the dialyzer, blood flow direction changeover means that is attached to the blood circuit for changing over the direction of the blood flow through the dialyzer from one direction to the other, a dialytic liquid circuit for feeding fresh dialytic liquid to the dialyzer, dialytic liquid flow direction changeover means that is provided on a part of the dialytic liquid circuit for reversing the direction of a dialytic liquid flow through the dialyzer to the direction of the blood flow, and control means for placing the dialytic liquid flow direction changeover means and the blood flow direction changeover means under intermittent changeover control.

According to the first aspect of the invention, the arterial blood circuit is coupled from the artery of a patient through a blood pump to the dialyzer, and the blood flow path changeover means is located between the blood pump and the dialyzer and is then coupled to the blood circuit. Then, the venous blood circuit for connecting the dialzyer to the patient is also coupled to the blood circuit by way of the blood flow path changeover means. The blood enters from the blood pump into the blood flow path changeover means. Both the arterial inlet and the venous outlet leading back to the patient are fixed, but both the feed port to the dialyzer and the discharge port from the dialyzer can be changed over (i.e. the feed portion can become the discharge port, and the discharge port can become the feed port). Intermittent changeover of these ports by the control means enables the direction of the blood flowing through the dialyzer to be changed over from one direction to the other.

According to the second aspect of the invention, the direction of the blood flowing through the dialzyer is intermittently changed over from one direction to the other by the blood flow path changeover means located in the blood circuit coupled to the dialyzer. Thus, the blood inlet and outlet in the dialyzer are constantly reversed, making blood coagulation unlikely to occur or, if blood coagulation occurs, making it possible to discharge it by blood flow inversion.

According to the third aspect of the invention, the dialytic liquid circuit feeds fresh dialytic liquid to the dialyzer. Then, it is possible to prevent the feeding back of the thrombus to the body, because the thrombus inflow preventing filter is located in the vicinity of the outlet in the blood circuit or the position through which the dialyzed blood returns into the body, and it is also possible to prevent contamination of the dialyzer with various bacteria, because the bacterium-eliminating or pyrogenic filter is located in the vicinity of the inlet in the dialytic liquid circuit.

According to the fourth aspect of the invention, the dialytic liquid flow path changeover means (e.g., three-way valves) F1 and F2 are located on feed (inlet) and discharge (outlet) lines of the dialytic liquid circuit, whereby the feed and discharge of dialytic liquid to and from the dialzyer 3 can constantly be changed over in the direction reverse to the flow of blood through the dialyzer. Then, electrical or other control means is provided to control the blood flow direction changeover means and the dialytic liquid flow direction changeover means, so that the directions of the respective flows can be changed over at a suitable interval.

BRIEF DESCRIPTION OF THE DRAWINGS

The present invention will now be explained, by way of example but not by way of limitation, with reference to the accompanying drawings, in which.

DETAILED EXPLANATION OF THE PREFERRED EMBODIMENTS

Figure 1:
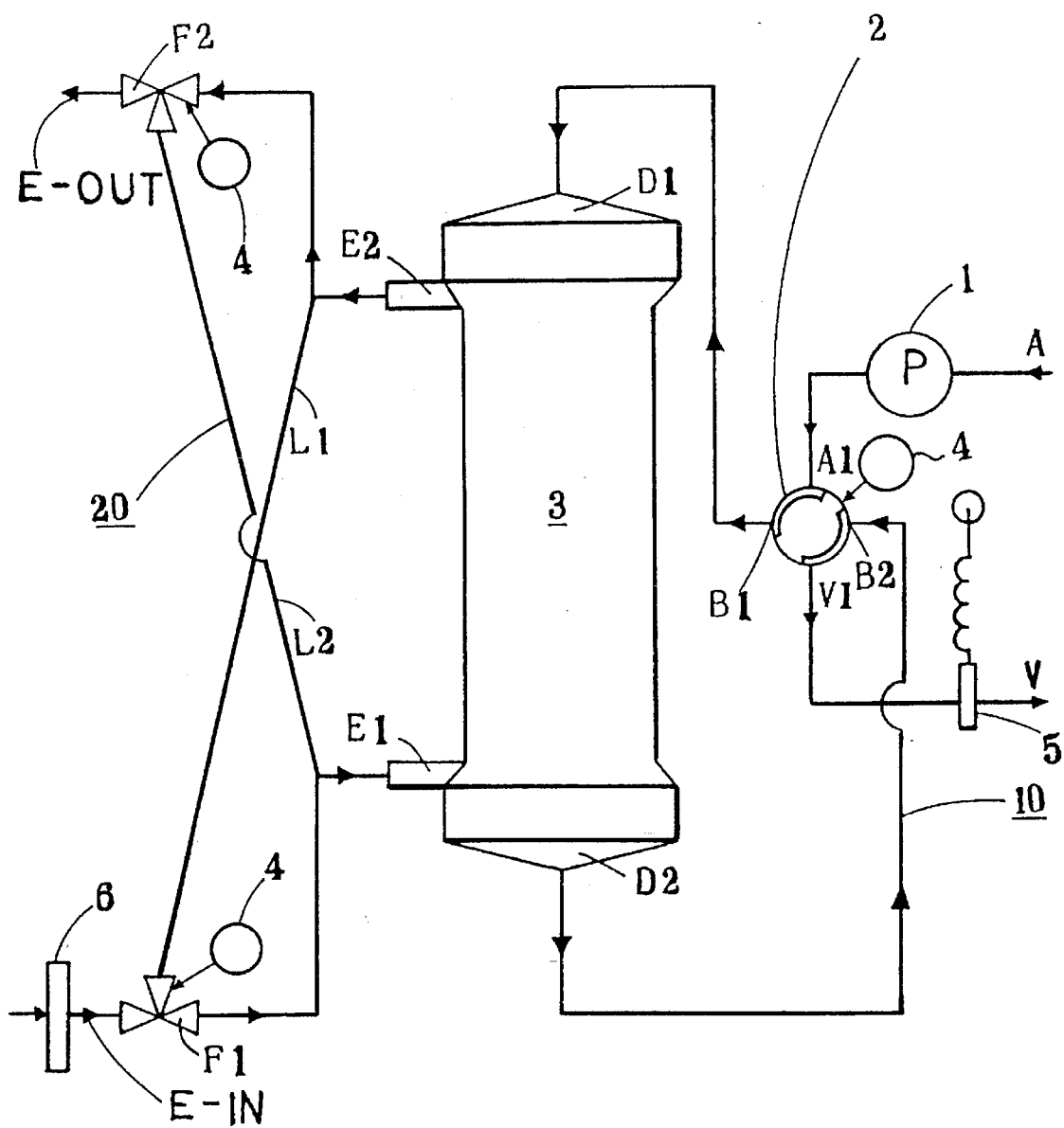
FIG. 1 is a schematic representation of a hemodialyzer unit in which blood- and dialytic liquid-flow path changeover means of the invention are incorporated.

The first embodiment of the invention will now be explained. A hemodialyzer unit includes a blood circuit 10 in which a blood pump 1 and a blood flow direction changeover means 2 are incorporated. This circuit is coupled to a dialyzer 3. The changeover means 2 changes over the direction of blood through the dialyzer from one direction to the other. Further, there is provided a control means 4 to place the changeover means 2 under intermittent changeover control. In addition, the hemodialyzer unit includes a dialytic liquid circuit 20 to feed fresh dialytic liquid to the dialyzer 3.

Referring then to the second embodiment of the invention, there is provided a method for changing over the direction of blood flow to a hemodialyzer unit, wherein a blood flow changeover means is coupled to a blood circuit 10 connected to a dialyzer 3, thereby intermittently changing over the direction of blood flow through the dialyzer 3 from one direction to the other.

In the ensuing description, the third embodiment of the invention will be explained. It is understood that this embodiment follows the first embodiment of the invention with the following exception. A bacterium-elimination or pyrogenic filter 6 is located in the vicinity of an inlet in the dialytic liquid circuit 20 for feeding fresh dialytic liquid to the dialyzer 3, and a thrombus inflow-preventing filter 5 is disposed in the vicinity of an outlet in the blood circuit 10 or a position through which the dialyzed liquid returns into the body.

In what follows, the fourth embodiment of the invention will be explained. This embodiment is identical to the first embodiment of the invention with the following exception. Dialytic liquid flow path changeover means (e.g., three-way valves) F1 and F2 are located on feed (inlet) and discharge (outlet) lines of the dialytic liquid circuit 20, whereby the feed and discharge of dialytic liquid to and from the dialzyer 3 can constantly be changed over to a direction reverse to the flow of blood through the dialyzer 3. Then, electrical or other control means 4 is provided to control the blood flow direction changeover means 2 and the dialytic liquid flow direction changeover means F1 and F2, so that the directions of the respective flows can be changed over at a suitable interval. It is understood that this feature of the invention may be applicable to the third embodiment as well as the fourth embodiment.

The operation of each of the embodiments of the invention mentioned above will now be explained. Blood guided out of the artery A of a patient by the blood pump 1 is first introduced into an arterial inlet A1 in the blood flow direction changeover means 2, and it is then guided from its outlet B1 to the dialzyer 3 through an inlet D1 therein. The blood then leaves an outlet D2 in the dialyzer 3, enters inlets B-2 in the blood flow path changeover means 2, and leaves through a venous outlet V1 and returns into the vein V of the patient. The dialytic liquid, on the other hand, leaves a dialytic liquid outlet E2, passes through the dialytic liquid flow direction changeover means F2 and is finally discharged through a dialytic liquid outlet E-OUT. As can be understood from the foregoing, lines L1 and L2 are not in communication with each other.

Figure 2:
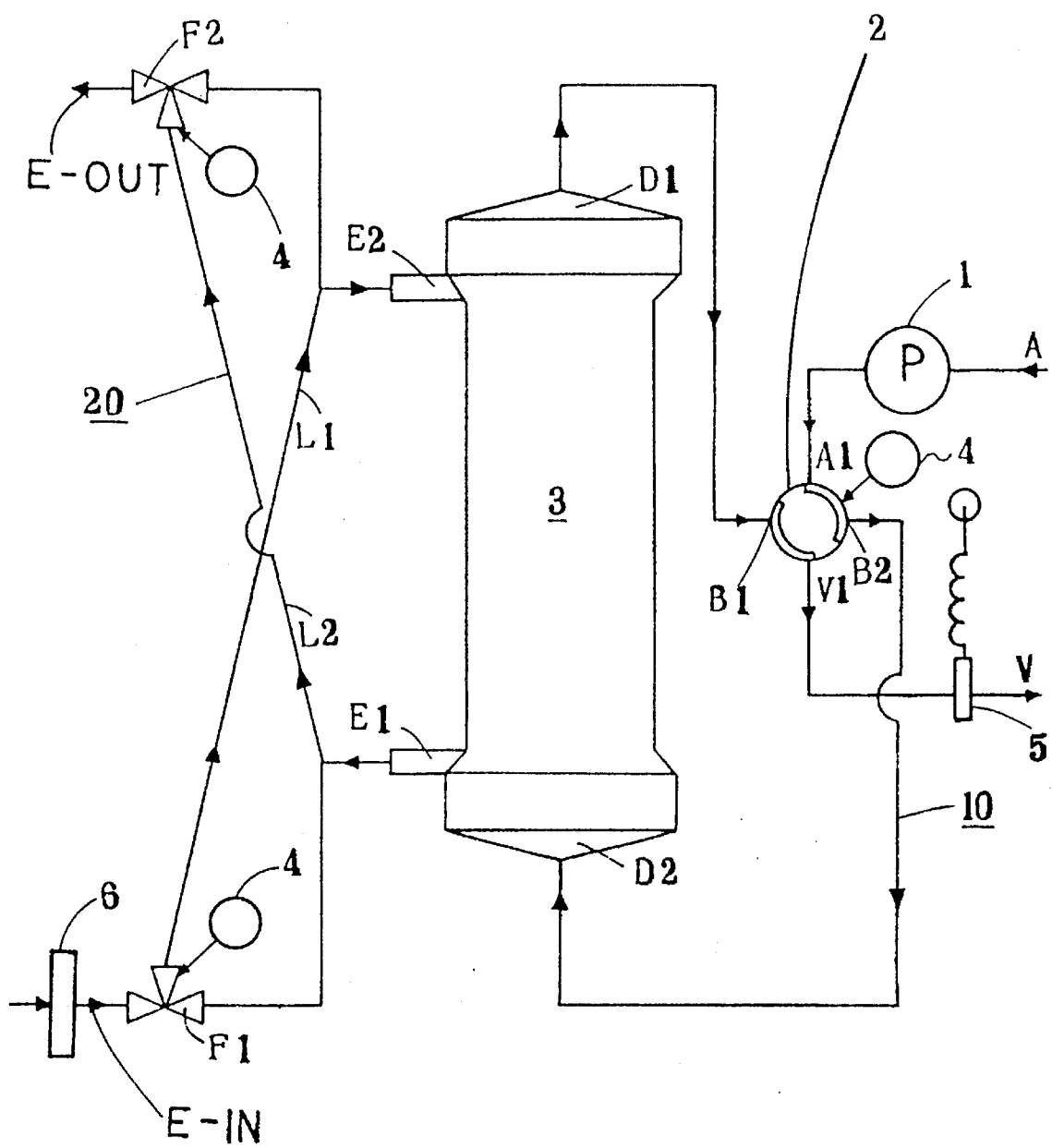
FIG. 2 is an illustration of how blood- and dialytic liquid-flow paths of FIG. 1 are changed over.
Figure 3:
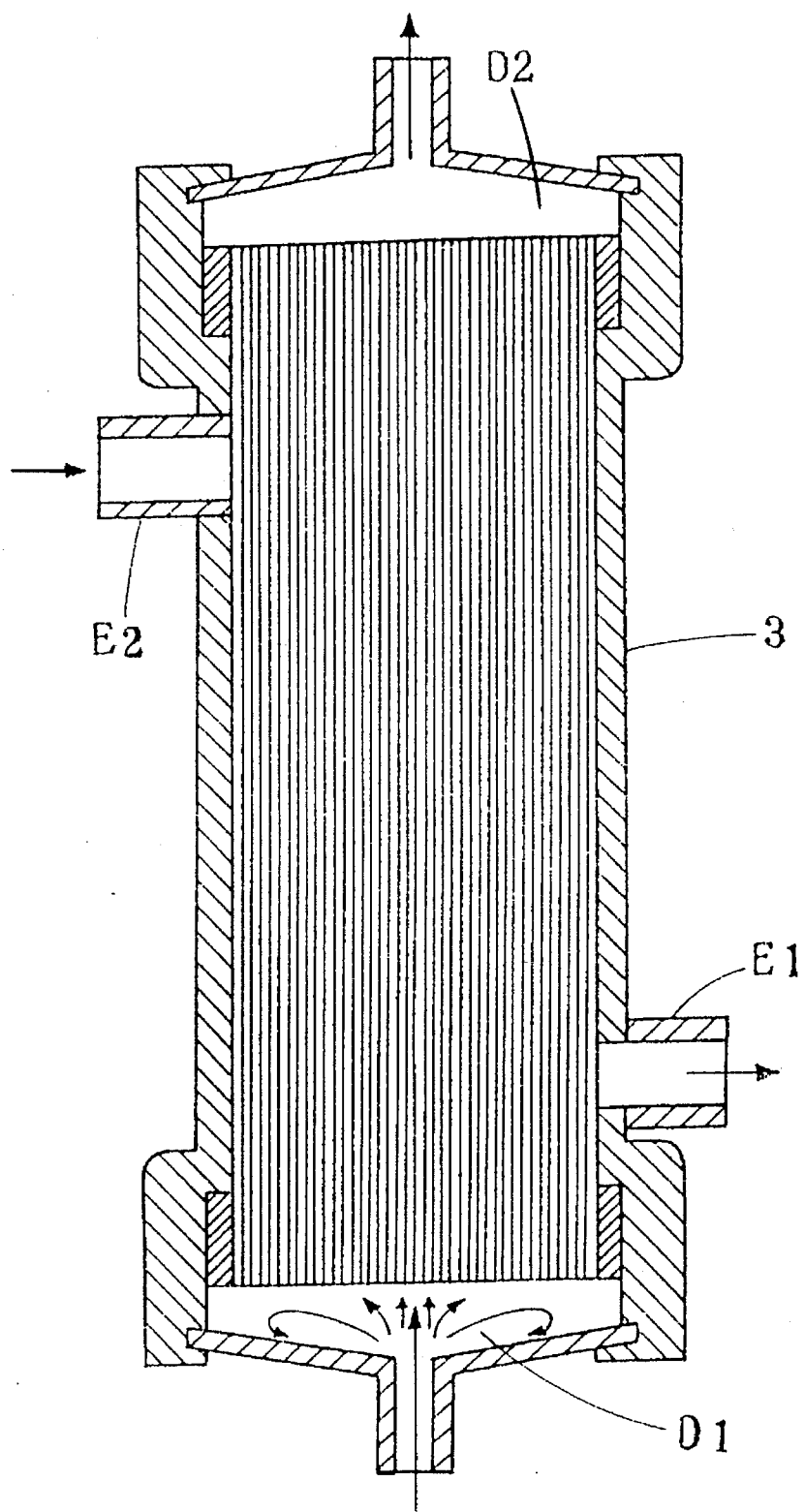
FIG. 3 is a side section of one embodiment of a dialyzer.

FIG. 2 is an illustration of how the flows of the blood and dialytic liquid of FIG. 1 are respectively reversed. At this time, the dialytic liquid passes from the dialytic liquid flow direction changeover means F1 through the line L1, enters through E2 into the line L1 and dialytic liquid flow direction changeover means F2 for discharge. According to this embodiment, the direction changeover of the blood and dialytic liquid flows can be simultaneously achieved, and the interval for changeover can be determined as desired.

The blood flow direction changeover device and method according to the invention, because of the device being constructed as mentioned above, have a number of merits.

For example the coagulation of blood in the dialyzer during hemodialysis can be inhibited to a large extent, the feeding back of blood after the completion of dialysis is easily achieved, and a great contribution is made to recycling (or re-use) of the dialyzer.

What is claimed is:

1. A hemodialysis device comprising:

a dialyzer having first and second blood flow ports and first and second dialytic liquid flow ports;

a blood flow circuit coupled to each of said first and second blood flow ports of said dialyzer and having an arterial inlet and a venous outlet;

a blood flow direction changeover means connected in said blood flow circuit for changing a blood flow direction through said dialyzer between a first blood flow direction in which blood flows into said dialyzer through said first blood flow port and out of said dialyzer through said second blood flow port, and a second blood flow direction in which blood flows into said dialyzer through said second blood flow port and out of said dialyzer through said first blood flow port;

control means for controlling said blood flow direction changeover means to intermittently change the blood flow direction through said dialyzer between said first blood flow direction and said second blood flow direction; and a dialytic liquid flow circuit coupled to said first and second dialytic liquid flow ports of said dialyzer.

2. A hemodialysis device as recited in claim 1, further comprising a dialytic liquid flow direction changeover means connected in said dialytic liquid flow circuit for changing a dialytic liquid flow direction through said dialyzer between a first dialytic liquid flow direction in which dialytic liquid flows into said dialyzer through said first dialytic liquid flow port and out of said dialyzer through said second dialytic liquid flow port, and a second dialytic liquid flow direction in which dialytic liquid flows into said dialyzer through said second dialytic liquid flow port and out of said dialyzer through said first dialytic liquid flow port; and control means for controlling said dialytic liquid flow direction changeover means to intermittently change the dialytic liquid flow direction through said dialyzer between said first dialytic liquid flow direction and said second dialytic liquid flow direction.

3. A hemodialysis method comprising:

providing a dialyzer having first and second blood flow ports and first and second dialytic liquid flow ports;

coupling a blood flow circuit, having an arterial inlet and a venous outlet, to each of said first and second blood flow ports of said dialyzer;

operating a blood flow direction changeover device connected in said blood flow circuit to intermittently change a blood flow direction through said dialyzer between a first blood flow direction in which blood flows into said dialyzer through said first blood flow port and out of said dialyzer through said second blood flow port, and a second blood flow direction in which blood flows into said dialyzer through said second blood flow port and out of said dialyzer through said first blood flow port; and coupling a dialytic liquid flow circuit to said first and second dialytic liquid flow ports of said dialyzer.

* * * * *